United States Patent [19]

Grell et al.

[11] 4,177,524

[45] Dec. 11, 1979

[54] MEDICAL SECUREMENT ELEMENT WITH ABRASIVE GRAINS ON THREAD SURFACE

[75] Inventors: Helmut Grell, Aalen; Heinz Scharbach, Plankstadt, both of Fed. Rep. of Germany

[73] Assignee: Pfaudler-Werke A.G., Schwetzingen, Fed. Rep. of Germany

[21] Appl. No.: 795,658

[22] Filed: May 10, 1977

[30] Foreign Application Priority Data

May 14, 1976 [DE] Fed. Rep. of Germany ...... 2621384

[51] Int. Cl.² .............................................. A61F 1/24
[52] U.S. Cl. .......................................... 3/1.9; 3/1.91; 3/1.913; 128/92 B; 128/92 C; 427/2
[58] Field of Search .................... 3/1.9–1.913; 128/92 C, 92 B, 92 CA, 92 BC; 32/10 A

[56] References Cited

U.S. PATENT DOCUMENTS

| | | | |
|---|---|---|---|
| 3,435,526 | 4/1969 | Brancato | 32/10 A |
| 3,787,900 | 1/1974 | McGee | 3/1.9 |
| 3,905,047 | 9/1975 | Long | 3/1.9 |
| 3,924,275 | 12/1975 | Heimke et al. | 3/1.912 |
| 3,971,073 | 7/1976 | Richards et al. | 3/13 |
| 3,987,499 | 10/1976 | Scharbach et al. | 3/1.91 |

OTHER PUBLICATIONS

"Development of Ceramic & Ceramic Composite Devices for Maxillofacial Applications" by T. D. Driskell, et al., Journal of Biomedical Materials Research Symposium, No. 2, part 2, 1972, pp. 345-361.

*Primary Examiner*—Ronald L. Frinks
*Attorney, Agent, or Firm*—Theodore B. Roessel; James A. Rich

[57] ABSTRACT

A medical securement element with a self-tapping screw thread is provided with biocompatible abrasive grains at the surface of the thread. The grains are preferably embedded in a layer of porcelain enamel on a metal substrate.

11 Claims, 7 Drawing Figures

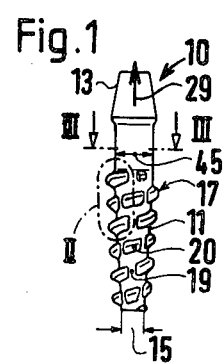
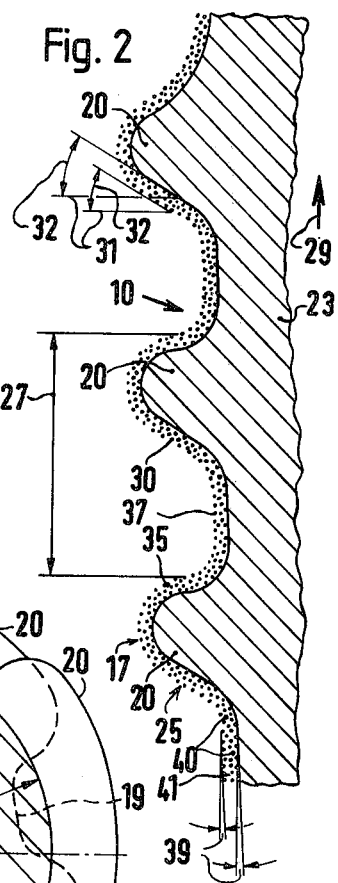
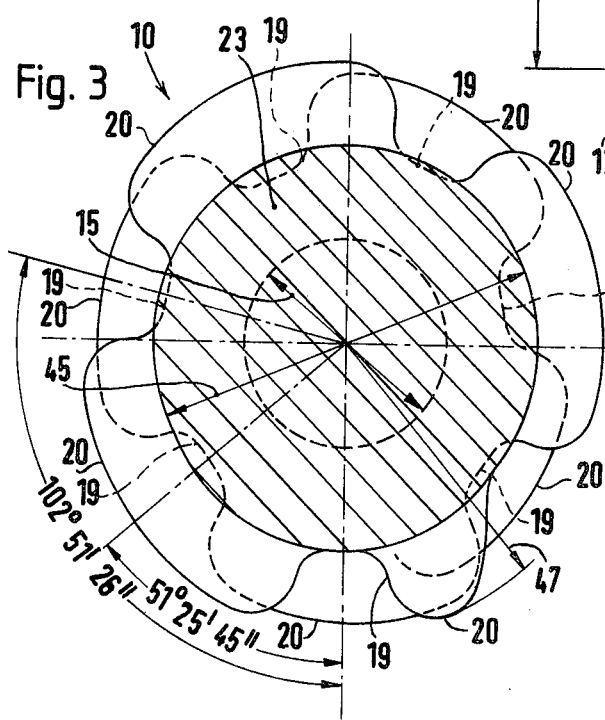

MEDICAL SECUREMENT ELEMENT WITH ABRASIVE GRAINS ON THREAD SURFACE

BACKGROUND OF THE INVENTION

This invention relates to a medical securement element with a self-tapping screw thread, subdivided by cut-out notches into thread segments, which engages a counterpart thread in a bone.

A known securement element of this kind (German Offenlegungsschrift No. 2,340,546, British Patent Application No. 28426/74), U.S. Pat. No. 3,987,499 consists of an enamelled anchoring part with a self-tapping external rounded screw thread. The anchoring part includes axially parallel through-going cut-out notches for the removal of bone chips and is screwed into the appropriate bone with a tool, such as a box spanner, by means of lateral surfaces. One disadvantage of this anchoring part is that it seeks the path of least resistance when being screwed in and can follow the soft tissue in the bone. As a result, the end position of the anchoring part is not defined accurately and its threads turns are finally located in the least load-bearing bone tissue. Another disadvantage is that the torque required for screwing this anchoring part into the bone is relatively high.

SUMMARY OF THE INVENTION

Objects of the present invention are to achieve a definite end position for the securement element, to achieve optimum utilization of the strength of the bone, and to reduce the torque required for insertion. These objects are achieved in accordance with the present invention in that at least the thread segments of the securement element, which preferably comprises a metal core or substrate coated with enamel, are provided with biocompatible abrasive grains at the surface of the thread. If desired, the whole of the surface of the securement element facing the bone can be provided with biocompatible abrasive grains.

According to a preferred embodiment of the invention, the abrasive grains are calcium hydroxyl apatite. These abrasive grains are sharp edged and are not only biocompatible, but also bioactive. This means that, after the operation, the material of the abrasive grains is resorbed by the surrounding tissue and used for desirable reformation of bone tissue around the securement element. Thus, pores are formed in the securement element, into which the reformed bone cells grow. In this way, a very desirable secondary fixation of the securement element in the bone occurs, so that the operation site can become fully loaded a mere two to three months after the operation. A partial loading is possible practically immediately after the operation, since the securement element positively locks into place and is connected to the bone without the disadvantage of bone cement. All this contributes to the desired early mobilization of the patient and thus to the avoidance of secondary diseases due to extended immobility.

The abrasive grains may also be quartz sand. The quartz sand is not resorbed by the tissue surrounding the bone, but instead forms a rough surface on the securement element to which the later growing bone tissue likewise finds good adhesion for secondary fixation.

The abrasive grains are preferably embedded in an enamel layer adhering to the surface of the metal substrate of the securement element, or to one or more enamel layers previously applied to the substrate. As used herein, enamel means a porcelain enamel, i.e., a vitreous or partially devitrified inorganic coating bonded to metal by fusion at a temperature above approximately 425° C. This type of enamel is ideally biocompatible and is therefore especially suitable as a carrier material for the abrasive grains.

Another object of this invention is to provide methods for providing body implants, such as securement elements, with biocompatible abrasive grains at the surface of the implant. In accordance with one embodiment of the invention, an enamel frit is ground, formed into an aqueous slurry or slip and then applied to the securement element or other implant. Relatively high melting biocompatible abrasive grains are then distributed or powdered upon the wet slip, after which the implant is heated or fired to fuse the enamel to the substrate. The melting point of the abrasive grains is high enough so that upon firing, they become securely embedded in the enamel layer but do not become molten. Thus, even after the final firing the sharpness of the abrasive grains is retained.

According to another embodiment of this invention, the relatively high melting abrasive grains are added to the grinding mill, in the final stages of grinding the enamel frit, and blended with the frit. The mixture is then applied to the securement element or other implant and fired to fuse the enamel. If desired, additional high melting grains can be applied to the moist slip after the slip has been applied to the substrate but prior to firing.

Other objects and advantages of this invention will be apparent from the following detailed description.

DRAWINGS

FIG. 1 shows a pin-like securement element in side view.

FIG. 2 shows the region II in FIG. 1 in cross-section and on an enlarged scale.

FIG. 3 shows a sectional view along lines III—III in FIG. 1 on an enlarged scale.

DETAILED DESCRIPTION

Figure 4:
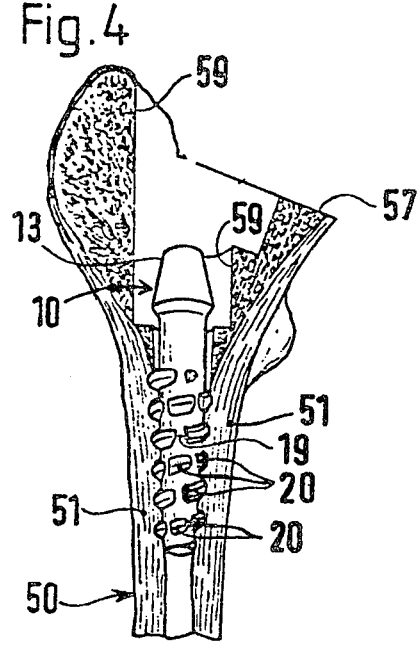
FIG. 4 shows a longitudinal section through the upper part of a thigh bone with an inserted securement element according to FIG. 1.

FIG. 1 illustrates a pin like securement element 10 with a downwardly tapering conical threaded core 11 and an upper mounting cone 13 for the support of further implant components. The threaded core 11 has a minimum threaded core diameter 15 at the bottom.

As may be seen in FIG. 2, the securement element 10 consists of a metal substrate 23 which is provided with a biocompatible abrasive surface 25, comprising abrasive grains 40 embedded in an enamel layer 41.

The securement element 10 is provided with a thread turn 17 which is sub-divided by means of cut-out notches 19 into a series of thread segments 20. In each successive row of thread segments in the direction of the longitudinal axis of the securement element, the thread segments are displaced in the circumferential or peripheral direction from the thread segments in each adjacent row. Preferably, the thread segements are displaced by half the distance between the midpoints of the adjacent thread segments from segments in adjacent rows. Thus, the threaded segments 20 are arranged "opposite" or aligned with the cut-out notches 19. In this way, the notches provide effective bond chip removal and the segments provide very uniform support around the entire periphery of the securement element. This promotes more reliable centering and anchoring of the securement element in the bone.

With a securement element having a conical thread, the distance between the midpoints of adjacent thread segments preferably increases from one thread segment to the next in the direction of increasing thread diameter. This keeps the thread segments and cut-out notches in adjacent rows aligned with each other, as specified above.

The conicity of the securement element 10, indicated in FIG. 2 by angle 39, may typically be 3.5°. However, depending upon the anatomical relationships, the securement element can be made cylindrical or in some other configuration.

The pitch of the thread turn 17 in FIG. 2 is indicated at 27. The direction of the tensile force to be transmitted through the securement element 10 in its installed position is indicated by an arrow 29. One surface 30 of each thread segment 20, arranged opposite to the direction of the arrow 29, forms a relatively large angle 32, such as 30°, with a horizontal 31. However, a surface 35 of each thread segment 20 arranged in the direction of the arrow 29 encloses a comparatively small angle, which can even be zero, with the horizontal. With this type of thread, commonly called a saw-tooth thread, the side 35 of each thread segment facing in the direction in which forces are to be transmitted by the securement element to the bone runs at least approximately at right angles to this direction. As a result, radially directed force components which would exert an expansive force upon a bone with a pin like securement element or a compressive force upon a bone with a sleeve like securement element are minimized.

The sawtooth threads also allow the formation of sectional surfaces of the thread segments as "supports of equal strength". The loads on the thread, which are mainly due to bending moments imposed on the securement thread segments 20 by the corresponding bond thread and vice versa, tend to increase relatively linearly from a minimum valve at the outermost point or apex of the thread to a maximum value near the base of the thread. Since the thickness and cross-sectional area of the thread increase from the apex to the base of the thread in roughly the same manner, the smaller cross-sectional or outer areas of the thread portion are under relatively small bending moments and the thicker portions are under larger bending moments. Thus, the sectional surfaces have roughly equal strength from apex to base.

Since the strength of the bone tissue is lower than that of the securement element 10, a thread base 37 of relatively large axial extent is made on the securement element 10 to provide the most equal loading possible on the thread segments 20 and the counterthread in the bone. Preferably, the ratio of the maximally stressed cross-sectional area of each segment, which is approximately the base area along which the thread segments 20 are joined to the remainder of the securement element 10, to the maximally stressed cross-sectional surface of the counterthread on the bone which cooperates with the respective thread segments is in the range from 1:1 to 0.1:1. Equal strength of the securement element thread and the bone counter-thread would be ideal. However, this would mean that the pitch of the thread turn 17 would be too large, because of the relatively low strength of the bone. A thread with too great a pitch can only be mounted with difficulty. Also when an axial load is subsequently exerted a loosening force results, that is, the connection no longer lies in the self-locking range. The suggested range of ratios forms a satisfactory compromise between strength and thread pitch.

In FIG. 3, the surface layer 25 shown in FIG. 2 has been omitted for better representation. FIG. 3 shows a maximum thread core diameter, which is also indicated in FIG. 1. Also, in FIG. 3, half of the maximum external thread diameter 47 is indicated. In particular, however, FIG. 3 shows the arrangement and distribution of a number of the thread segments 20 and the cut-out notches 19 between the segments.

FIG. 4 shows the pin-like securement element 10 in the final position of its mounting in the upper part of a thigh bone 50. The thread portions 20 have become embedded and firmly located in the corticalis 51 of thigh bone 50.

Figure 5:
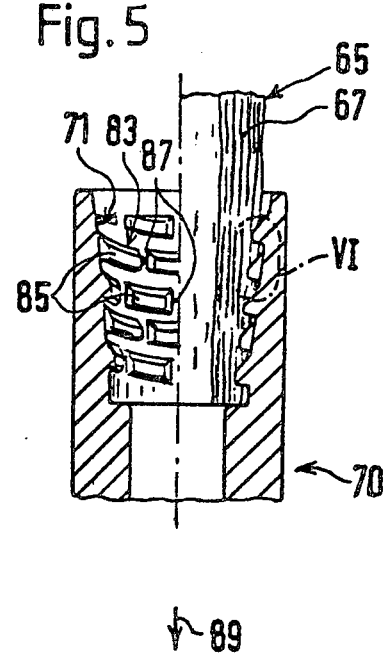
FIG. 5 shows a sleeve-like securement element partially in section, together with a tubular bond stump.

FIG. 5 shows a bone 65, e.g., an upper arm bone, the corticalis 67 of which has previously been shaped downwardly and externally as a slightly tapering cone. A sleeve like securement element 70, the inner surface 71 of which is abrasively active and biocompatible, is screwed on the bone 65.

Figure 6:
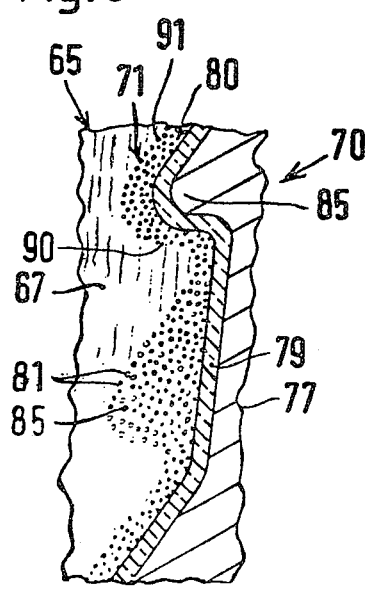
FIG. 6 shows the region VI in FIG. 5 on an enlarged scale.

FIG. 6 shows details of the surface structure of the sleeve like securement element 70 which have been omitted from FIG. 5. for greater clarity of illustration. A metal substrate 77 is provided over its whole surface with a rigidly-adherent enamel layer 79 which is completely impervious with respect to body fluids. A further enamel layer 80 is fused to the enamel layer 79 and serves as the carrier material for abrasive grains 81 embedded therein.

The sleeve like securement element 70 also has a thread turn 83, divided into a series of thread segments 85, which are separated from one another by respective cut-out notches 87. An arrow 89 indicates the direction of operative loading (tensile force) of the unit formed by the bone 65 and the securement element 70. A surface 90 of any thread segment 85 facing in the direction of the force 89 runs approximately at right angles to the direction of the force, whereas the other surface 91 of any thread segment 85 forms an angle with the horizontal. This thread is thus also of the so-called saw-tooth type.

Figure 7:
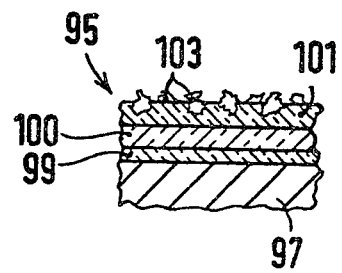
FIG. 7 shows an enlarged sectional view through part of an implant, illustrating the embedment of abrasive grains in an enamel coating.

FIG. 7 shows a part of an implant 95, represented in cross-section, which comprises a metal substrate 97 provided with an enamel ground layer 99 and a rigidly-adherent enamel covering layer 100 which is absolutely impervious with respect to body fluids over the enamel ground layer 99. The enamel covering layer 100 may consist of partially crystallized or devitrified enamel. This allows the characteristics of the enamel layer to be varied over wide limits to suit the requirements desired.

On the enamel covering layer 100, a further enamel layer 101 is fused, which serves as the carrier material for abrasive grains 103 embedded therein. Layer 101 may have a thickness, for example, of 0.3 to 0.6 mm. The abrasive grains 40 may typically comprise 20% to 60% by weight of layer 101, with the balance being enamel matrix. Preferably, the abrasive grains 103 have a maximum grain size of about 0.7 mm. This improves conditions for growth of reformed bone tissue into the pores formed in the securement element when bioactive abrasive grains such as calcium hydroxyl apatite are used. Typically the abrasive grains may range in size from 0.2 to 0.4 mm.

The implant 95 can be either a pin-like securement element like the securement element 10 or a sleeve-like securement element like the securement element 70. However, any other type of implant having the aforementioned features and advantages may be manufactured in the previously described manner.

EXAMPLE OF PREPARATION

The metal substrate of an implant is prepared, for example, from a material having Alloy Number 2.4631 according to DIN 17007 (Ni Cr 20 Ti Al material) and is prepared in the usual way for the enamelling process, by pickling or sand-blasting. A crystallizable enamel mixture according to Table I is melted, fritted, ground, applied, fired and finally subjected to partial crystallization by heat treatment, in the known manner described in German Auslegeschrift No. 1,291,597 and U.S. Pat. No. 3,368,712.

TABLE I

| Oxides | Weight percent of the total coating composition |
| --- | --- |
| $SiO_2$ | 56.02 |
| $Na_2O$ | 6.50 |
| $Li_2O$ | 10.38 |
| $Al_2O_3$ | 5.46 |
| $TiO_2$ | 16.60 |
| $B_2O_3$ | 4.50 |
| SrO | 1.50 |

The frit is prepared in the form of a thin aqueous slurry, referred to in the enamelling art as a slip, and is applied by spraying. The ultimate enamel thickness desired is achieved in some instances only after multiple firing. Controlled crystallization is only then allowed to take place. With the above-mentioned metal substrate, the provision of an enamel ground coat below the crystallizable enamel can be dispensed with. If such a ground coat is recommended, however, its composition can be in accordance with Table II below.

TABLE II

| Oxides | Weight percent |
| --- | --- |
| $SiO_2$ | 48.5 |
| $Na_2O$ | 14.7 |
| $K_2O$ | 4.4 |
| $Al_2O_3$ | 6.4 |
| $MnO_2$ | 1.7 |
| $B_2O_3$ | 16.0 |

The implant coated with a partially crystallized enamel layer is then examined for contact zones with the metal substrate by means of high voltage (3 to 10 kV), or by current measurement methods after immersion in an electrolyte. If no faults are found, a further enamel layer is applied as the carrier material for the abrasive grains, made up for instance in accordance with Table III below, which gives the details of four known highly acid-resistant enamels.

TABLE III

|  | 1 | 2 | 3 | 4 |
| --- | --- | --- | --- | --- |
| $SiO_2$ | 65.1 | 66.9 | 51.1 | 65.3 |
| $Al_2O_3$ | 3.5 | 3.0 | 2.6 | 3.1 |
| $B_2O_3$ | 2.0 | — | 9.4 | — |

TABLE III-continued

|  | 1 | 2 | 3 | 4 |
| --- | --- | --- | --- | --- |
| $K_2O$ | 2.6 | 18.7 | 1.3 | 1.5 |
| $Na_2O$ | 19.1 | 18.7 | 17.3 | 18.1 |
| CaO | 7.7 | 7.3 | 6.5 | 6.9 |
| MgO | — | — | — | 5.1 |
| ZnO | — | 1.1 | 11.8 | — |
| $Li_2O$ | — | 3.0 | — | — |

This latter enamel layer can be mixed with the abrasive grains in a homogeneous distribution and/or the abrasive grains can be distributed or powdered on prior to firing and are thus retained in the ultimate surface layer. The abrasive grains can be distributed with 40% to 80% by weight of dry enamel powder. In this simple way, a desired distribution of the abrasive grains upon the surface can be achieved.

Of course, those skilled in the art may make numerous modifications in the securement elements and production techniques described above within the scope of this invention, which is defined by the following claims.

We claim:

1. A medical securement element for engagement with a counterthread in a bone, comprising a self-tapping screw thread with biocompatible abrasive grains at the surface of the thread.

2. A securement element according to claim 1 wherein the abrasive grains comprise calcium hydroxyl apatite.

3. A securement element according to claim 1 wherein the abrasive grains comprise quartz sand.

4. A securement element according to claim 1 wherein the abrasive grains have a maximum grain size of 0.7 mm.

5. A securement element according to claim 4 wherein the abrasive grains have a grain size ranging from 0.2 to 0.4 mm.

6. A securement element according to claim 1 wherein the abrasive grains are embedded in an enamel layer.

7. A securement element according to claim 6 wherein the thread is covered with a layer comprising 20% to 60% by weight of said abrasive grains, the balance of said layer being enamel matrix.

8. A securement element according to claim 1 wherein the thread is subdivided by cut-out notches into thread segments and the thread segments in each row of segments are displaced circumferentially in relation to the thread segments of each adjacent row.

9. A securement element according to claim 8 wherein each thread segment is displaced circumferentially from thread segments in adjacent rows by one-half the distance between the midpoints of adjacent thread segments, whereby each thread segment is aligned with the cut-out notches in adjacent rows.

10. A securement element according to claim 8, having a conical thread, wherein the distance between midpoints of adjacent thread segments increases from one thread segment to the next in the direction of increasing thread diameter.

11. A securement element according to claim 1 wherein the thread is subdivided by cut-out notches into thread segments and the ratio of the maximally stressed cross-sectional surface of each thread segment to the area enclosed by a first line along the apex of said thread segment, a second line along the apex of an axially adjacent thread segment, a third line extending through one end of said thread segment at right angles to said first line, and a fourth line extending through the other end of said thread segment at right angles to said first line is in the range from 1:1 to 0.1:1.

* * * * *